United States Patent [19]

Nestler

[11] Patent Number: 4,547,583
[45] Date of Patent: Oct. 15, 1985

[54] PROCESS FOR ESTERIFYING PHENOL-CONTAINING CARBOXYLIC ACIDS

[75] Inventor: Hans J. Nestler, Königstein, Fed. Rep. of Germany

[73] Assignee: Hoechst Aktiengesellschaft, Frankfurt am Main, Fed. Rep. of Germany

[21] Appl. No.: 657,571

[22] Filed: Oct. 3, 1984

[30] Foreign Application Priority Data

Oct. 5, 1983 [DE] Fed. Rep. of Germany ....... 3336199

[51] Int. Cl.$^4$ ............................................. C07C 69/76
[52] U.S. Cl. .................................... 560/061; 560/67; 560/75
[58] Field of Search ............................... 560/61, 75, 67

[56] References Cited

U.S. PATENT DOCUMENTS

| 3,247,240 | 4/1966 | Meier et al. ........................... 560/75 |
| 4,001,299 | 1/1977 | Dexter et al. ......................... 560/75 |
| 4,228,297 | 10/1980 | Haeberli et al. . | |

FOREIGN PATENT DOCUMENTS

| 288839 | 4/1967 | Australia ............................... 560/75 |
| 102920 | 3/1984 | European Pat. Off. .............. 560/75 |
| 794229 | 4/1958 | United Kingdom .................... 560/75 |

Primary Examiner—Paul J. Killos
Attorney, Agent, or Firm—Curtis, Morris & Safford

[57] ABSTRACT

Carboxylic acids containing phenol groups are esterified by means of ($C_1$–$C_3$)-alcohols in the presence of acid catalysts without the phenolic hydroxyl groups being esterified at the same time by continuously metering an excess of a water-containing ($C_1$–$C_3$)-alcohol into a boiling hot solution or suspension of the phenol-containing carboxylic acid and of the catalyst in a non-water-miscible solvent (for example xylene) and at the same time distilling off a ternary solvent/alcohol/water mixture via a water separator, the metering rate being such that an aqueous bottom phase separates out in the receiving flask and the water content of the alcohol being so apportioned as not to breach the bottom limit of 0.1% or the upper limit of 1% (based on the contents of the reaction vessel) at any time in the course of the reaction. In this process, the esterification products are obtained free of major impurities and frequently can be used further without further purification.

4 Claims, No Drawings

PROCESS FOR ESTERIFYING PHENOL-CONTAINING CARBOXYLIC ACIDS

Whereas the selective alkylation of an aliphatic or aromatic carboxylic acid to its ester usually presents no problems even if alcoholic hydroxyl groups are present in the same molecule, this reaction is technically demanding in the case of carboxylic acids which contain phenolic hydroxyl groups in the same molecule. Owing to the fact that the carboxyl function and the phenol function are of comparable acidity and hence both nucleophilic, the esterification of the carboxylic acids is always accompanied by an occasionally appreciable etherification of the phenolic group, in particular when, in order to obtain the maximum degree of esterification, use is made of so-called "strong" alkylating agents, such as, for example, dialkyl sulfates, trialkyloxonium salts, diazoalkanes, alkylsulfonic and arylsulfonic acid esters or even alkyl halides in the presence of silver ions.

If milder alkylating conditions are used, for example if the carboxylic acids are reacted with alcohols in the presence of catalytic amounts of mineral acids, aromatic sulfonic acids or ion exchange resins, it is true that the phenolic groups are preserved unchanged, but, as is known, the esterification reaction leads only to equilibrium conversion; the reaction is prevented from going to completion by the water which is formed in the course of the reaction.

The customarily chosen way of removing the water of reaction from the esterification mixture, namely, for example, azeotropic distillation or the presence of entraining agents, usually fails in the case of the technically interesting low-boiling alcohols methanol, ethanol, n-propanol and isopropanol. The matter is further complicated by the fact that phenolic ether formation makes a marked reappearance as a secondary reaction to any attempt to remove as much of the water as possible. Moreover, under these conditions the phenol-containing carboxylic acids are frequently additionally involved in a polycondensation which produces unwanted high molecular weight byproducts.

These esterification batches, which did not go to completion or contain byproducts, are difficult to work up on the following grounds:
1. Because of the phenol group which is also present the customary alkaline extraction for removing unreacted acid cannot be used.
2. Any aqueous working-up procedure is hampered by the fact that the starting materials and end products are bifunctional and amphipolar compounds which frequently promote the formation of emulsions. If the medium is at an alkaline pH, in addition, the esters formed are easily hydrolyzed back into their components.
3. Working up by fractional distillation must be ruled out in most cases because the boiling points of main products and byproducts are too close together and because the phenol-containing carboxylic acid esters are relatively highly heat-sensitive.

The present state of the art of trying to overcome these problems in the esterification of phenol-containing carboxylic acids comprises carrying out the reaction of the acid with the particular alcohol in a plurality of stages under mild reaction conditions; in the final stage the alcohol is usually in water-free form to complete the conversion. However, this method is complex, costly in terms of time and energy, and, if implemented on an industrial scale, requires in addition the operation of a plant for absolute alcohol.

From the above remarks there is thus a need to determine conditions under which phenol-containing carboxylic acids can be converted into their lower alkyl esters in a single-stage reaction. This reaction should proceed so completely and selectively as to largely avoid producing the abovementioned byproducts and hence to make it possible to dispense with subsequent working-up and purifying operations.

This object is achieved according to the invention by continuously metering an excess of a water-containing $(C_1-C_3)$-alcohol into a boiling hot solution or suspension of the phenol-containing carboxylic acid and of the catalyst in a non-water-miscible solvent and at the same time distilling off a ternary solvent/alcohol/water mixture via a water separator, (a) the metering rate being such that an aqueous bottom phase separates out in the receiving flask and (b) the water content of the alcohol being so apportioned as not to breach the bottom limit of 0.1% or the upper limit of 1% (based on the contents of the reaction vessel) at any time in the course of the reaction.

The present invention accordingly achieves the stated object through the combination of two measures:
1. The continuous addition of small amounts of water which, surprisingly, has the effect of preventing the secondary reactions which normally occur under the drastic reaction conditions, such as etherification of the free phenol groups and polycondensation of the phenol-containing carboxylic acids. 2. The rapid continuous removal of the water which is formed in the course of the reaction. In the presence of the $(C_1-C_3)$-alcohols which are miscible with water in any ratio and have a solubilizing action this is only possible by ensuring that certain alcohol concentrations in the reaction mixture (for example about 15% by weight in the case of ethanol if xylene is used as the solvent) are not exceeded, so that the water separated at the receiving flask forms the bottom phase and there is no reflux of water into the reaction vessel. The simplest way of achieving this is to employ part-flow operation in which the alcohol is continuously replenished at the rate at which it is consumed by the esterification reaction. If excessively high alcohol concentrations occur in the reaction mixture as a result of excessively fast metering or an insufficiently low rate of reaction, this has the effect of preventing the formation of two phases in the water separator (necessary for separating off the water), so that water runs back into the reaction vessel. Consequently the reaction no longer proceeds as intended.

The combination of these measures has the effect of constantly maintaining in the reaction vessel a low steady-state water concentration which, although preventing the undesirable secondary reactions from taking place to any extent, permits the main reaction, viz. the desired esterification, to take place virtually unhindered.

The characteristic feature of the process according to the invention is the relatively high reaction temperature—made possible by the fact that neither the alcohol component nor the water are present in the reaction mixture in major concentrations. The high temperature is responsible for the fact that the rate of reaction is distinctly higher than is generally customary with esterifications. Times of 1–2 hours for the reaction are sufficient in the majority of cases. The yields are above 90% of theory or, in many cases, even above 95% of theory.

The water required for maintaining the steady-state water concentration in the reactor is customarily metered in in the form of a mixture with the alcohol for the esterification. The most suitable alcohol-water ratio for the various starting materials and solvents can be determined by means of simple preliminary experiments. The water content of the alcohols can be varied within wide limits (about 3–25%). It is thus even possible to use alcohols obtained, for example, by working up aqueous solutions. It is thus a further advantage of the process that there is no need to use water-free alcohols.

The process according to the invention generally produces the esterification products in excellent purity. Usually the residual free acid content is below 2% and phenolic ether impurities below 1%.

As a particular advantage the esterification reaction can also be carried out continuously. The residence times in the reactor are then usually below 1 hour.

The process which has been described is thus a simple, rapid and economical method for preparing phenol-containing carboxylic acid esters. The crude products produced by this highly selective reaction can usually be used further without further purification.

The starting materials for the process according to the invention can be carboxylic acids of the formula I which contains a hydroxyl group in ortho-, meta- or para-position on the aromatic moiety.

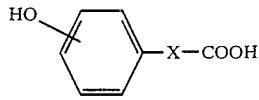

In the formula, X denotes a single chemical bond or a straight-chain or branched aliphatic saturated or mono-unsaturated or diunsaturated grouping of preferably 1–4 carbon atoms which is bonded to the ring either directly or by way of an oxygen or sulfur atom.

Examples of some customary phenol-containing carboxylic acids are 2-, 3- or 4-hydroxybenzoic acid, 2-, 3- or 4-hydroxyphenylacetic acid, 2-, 3- or 4-hydroxyphenylbutyric acid, 2-(2-hydroxyphenoxy)-propionic acid, 2-(3-hydroxyphenoxy)-propionic acid, 2-(4-hydroxyphenoxy)-propionic acid, 3-(4-hydroxyphenoxy)-propionic acid, 2-((4-hydroxyphenoxy)-butyric acid, 4-((4-hydroxyphenoxy)-butyric acid, 2-, 3- or 4-hydroxycinnamic acid.

If the aliphatic moiety of the molecule contains chiral centers, it will be readily understood that all existing sterioisomers or mixtures thereof can be subjected to the esterification according to the invention in the same way without racemization taking place.

Industrially important examples of the non-water-miscible, inert solvents are: preferably aromatics having boiling points between 80° and 145°, such as benzene, toluene or xylene (including as an industrial mixture of isomers), chlorinated aromatics, such as chlorobenzene, halogenated hydrocarbons, such as chloroform and trichloroethylene, and ($C_5$–$C_8$)-paraffins or mixtures thereof.

The catalysts are preferably sparingly volatile mineral acids, such as sulfuric or phosphoric acid; yet it is also possible to use sulfonated aromatics (for example toluenesulfonic acid) or acid ion exchange resins. Volatile acids, for example hydrogen chloride, which can, in principle, likewise be used as catalysts, are, in practice, frequently carried out together with the water of reaction and hence are of only limited effectiveness.

The synthesized esters of phenol-containing carboxylic acids are bifunctional compounds with a free phenol group and hence are of wide interest in preparative organic chemistry. They are, moreover, important precursors, intermediates and end products in pharmaceutical chemistry, plant protection chemistry, dyestuff chemistry and in the field of textile assistance, emulsifiers and other surface-active substances.

There now follow some examples and counter-examples which explain the invention in more detail and reveal the advantages of the new esterification method.

EXAMPLE 1

0.5 ml of concentrated sulfuric acid is added to a mixture of 7.6 g of 4-hydroxyphenylacetic acid and 50 ml of xylene in a flask which is equipped with a reflux condenser and a water separator, and the mixture is heated with stirring to 120° C. A mixture of 30 ml of xylene, 52 g of n-propanol and 5.2 g of water is added dropwise in the course of 80 minutes, and at the same time 74 g of distillate are removed from the refluxing solution by way of the water separator. This solvent mixture forms an aqueous bottom phase, which amounts to 1.7 g. After the addition is complete the reaction mixture is analyzed by gas chromatography and produces the following values (without solvent portions):

| | |
|---|---|
| n-propyl 4-hydroxyphenylacetate | 97.8% |
| n-propyl 4-n-propyloxyphenylacetate | 0.4% |
| 4-hydroxyphenylacetic acid | 1% |

The reaction mixture is worked up by washing with water or a dilute aqueous sodium hydrogencarbonate solution and evaporating the organic solvent under reduced pressure. The yields of ester in virtually all cases above 90–95% of theory. The product can be used for many purposes without further purification.

COMPARATIVE EXAMPLE 1

7.6 g of 4-hydroxyphenylacetic acid are esterified with n-propanol under the same conditions as in Example 1, except that in this case no water is added, affording as the distillate 67 g of solvent mixture, from which an 0.8 g aqueous bottom phase separates off. Analysis by gas chromatography produces the following values (without solvent portions) for the reaction mixture at the end of the addition of xylene/n-propanol:

| | |
|---|---|
| n-propyl 4-hydroxyphenylacetate | 89.6% |
| n-propyl 4-n-propyloxyphenylacetate | 1.5% |
| 4-hydroxyphenylacetic acid | 1% |

EXAMPLE 2

27.2 g of 4-hydroxybenzoic acid are suspended in 200 ml of xylene, and 2 ml of concentrated sulfuric acid are added. The mixture is heated to 125° C., and 43 g of 90% strength aqueous ethanol are then metered in in the course of 90 minutes. At the same time, 40 g of solvent mixture are distilled off via the water separator. The reaction temperature drops temporarily to about 120° C. On further refluxing the temperature gradually climbs back to 123° C. An analysis by gas chromatography is carried out after 14 hours. Result (without solvent portion):

| ethyl 4-hydroxybenzoate | 93.2% |
|---|---|
| 4-hydroxybenzoic acid | 2.0% |

Ethyl 4-ethoxybenzoate was not detectable. The reaction batch can be worked up by conventional methods. The yield is 90% of theory.

EXAMPLE 3

A suspension of 9.1 g of 2-(4-hydroxyphenoxy)propionic acid in 50 ml of xylene is introduced into a stirred flask which is equipped with a reflux condenser and a water separator. After addition of 0.5 ml of concentrated sulfuric acid the mixture is raised to 125° C., and 44.0 g of aqueous ethanol (water content 9% by weight) are then added dropwise at this temperature in the course 50 minutes. The solvent mixture which distils off during this period is removed via the water separator. A total distillate amounts to 67 g of a xylene/ethanol-water mixture, from which an aqueous bottom phase of 2.0 g separates off. In order to keep a constant amount of liquid in the reaction flask, a further 25 ml of xylene are metered in in the course of the reaction. Analysis by gas chromatography of the distillable portions of the crude product (without solvent) produces the following values:

| ethyl 2-(4-hydroxyphenoxy)-propionate | 92.18% |
|---|---|
| ethyl 2-(4-ethoxyphenoxy)-propionate | 1.79% |
| 2-(4-hydroxyphenoxy)-propionic acid | 1.57% |

EXAMPLE 3

9.1 g of 2-(4-hydroxyphenoxy)-propionic acid in 50 ml of a xylene are esterified in the presence of 0.5 ml of concentrated sulfuric acid by adding 40.0 g of anhydrous ethanol, under analogous conditions to those in Example 3. Again the volume in the flask is made up by metering in a further 25 ml of xylene. In the course of this experiment, a distillate of 60 g of solvent distils over in the course of 50 minutes, 1.4 g of this mixture forming an aqueous bottom phase.

Analysis by gas chromatography of the distillable portions of the crude product (without solvent):

| ethyl 2-(4-hydroxyphenoxy)-propionate | 91.95% |
|---|---|
| ethyl 2-(4-ethoxyphenoxy)-propionate | 4.53% |
| 2-(4-hydroxyphenoxy)-propionic acid | <0.1% |

The crude product solutions are worked up in the same way in both experiments, using known methods: after the sulfuric acid has been removed by extracting the xylene solution with water or a dilute solution of sodium hydrogencarbonate in water, the organic solvent is removed by distillation under reduced pressure. The yields of esterification product are of the order of 95% of theory.

EXAMPLE 4

Batchwise procedure—optimized conditions (apparatus as in Example 3).

A suspension of 9.1 g of 2-(4-hydroxyphenoxy)propionic acid in 50 ml of xylene has 0.5 ml of concentrated sulfuric acid added to it and is heated to 120° C. The water separator mounted on the apparatus contains a mixture of xylene and ethanol in the ratio of 5.67:1 from the preceding experiment. 22.0 g of 91% by weight strength aqueous ethanol are added dropwise to the reaction mixture in the course of 60 minutes. A clear solution forms after about 10 minutes of reaction. The solvent distillate which passes over flows back into the reaction flask by way of the water separator. In the course of the reaction 4.4 g of aqueous bottom phase separate off in the water separator; this water is not returned into the reactor. Analysis by gas chromatography of the distillable portions after the ethanol has been added produces the following values (without solvent portion):

| ethyl 2-(4-hydroxyphenoxy)-propionate | 96.51% |
|---|---|
| ethyl 2-(4-ethoxyphenoxy)-propionate | 0.48% |
| 2-(4-hydroxyphenoxy)-propionic acid | 0.45% |

The yield of isolated crude material after the sulfuric acid has been washed out and the solvent has been separated off is over 100%; if the measured ester contents are taken into account the yields are between 95 and 98% of theory in serial experiments.

EXAMPLE 5

Continuous procedure.

A 1 liter reaction vessel equipped with a reflux condenser, a water separator and an overflow is continuously charged with:

246 g/h of a warm 35% by weight strength solution at about 70° C. of 2-(4-hydroxyphenoxy)-propionic acid in a xylene/ethanol mixture with an ethanol content of 8% by weight. The organic acid is a technical-grade crude product and contains minor amounts of other substances;

270 g/h of xylene (technical-grade mixture of isomers)
4 g/h of 96% strength sulfuric acid
40 g/h of 95.8% strength aqueous ethanol.

This mixture is heated with stirring to 125° C. and begins to boil vigorously. The water-containing phase which separates off in the water separator as the bottom phase is continuously withdrawn, while the top phase continuously flows back into the reaction vessel. The overflow attached to the reactor is adjusted so that a constant amount of about 600 ml is inside the flask. When steady-state conditions have become established, 40 g/h of bottom phase can be taken out of the water separator and are found to have a composition of 6 parts of ethanol, 3 parts of water and 1 part of xylene. At the same time 520 g/h of a xylene solution containing on average 19.5% by weight of ethyl 2-(4-hydroxyphenoxy)-propionate are obtained at the overflow of the reactor; this corresponds to a yield of 97% of theory.

The throughput chosen in the example means that the residence time is about 1 hour. Residence times as short as 30 minutes are possible with virtually identical success. In a test run the experiment described was carried out continuously for a period of 40 hours. Four analytical samples taken at regular intervals were found to contain the following amounts (in parts by weight relative to 100 parts by weight of ethyl 2-(4-hydroxyphenoxy)-propionate for the typical byproducts:

ethyl 2-(4-ethoxyphenoxy)-propionate: 0.14; 0.33; 0.13; 0.31

2-(4-hydroxyphenoxy)-propionic acid: 1.73; 1.96; 1.33; 1.98

The reaction product is worked up conventionally.
All percentages are by weight.

I claim:

1. A process for esterifying carboxylic acids containing phenol groups by means of ($C_1$–$C_3$)-alcohols in the presence of acid catalysts without simultaneous esterification of the phenolic hydroxyl groups, which comprises continuously metering an excess of a water-containing ($C_1$–$C_3$)-alcohol into a boiling hot solution or suspension of the said carboxylic acid and of the catalyst in a non-water-miscible solvent and at the same time distilling off a ternary solvent/alcohol/water mixture via a water separator, (a) the metering rate being such that an aqueous bottom phase separates out in the receiving flask and (b) the water content of the alcohol being so apportioned as not to breach the bottom limit of 0.1% or the upper limit of 1% (based on the contents of the reaction vessel) at any time in the course of the reaction.

2. The process as claimed in claim 1, wherein the solvent loss caused by distilling off the solvent is made up during the reaction by adding solvent.

3. The process as claimed in claim 1, wherein the solvent is an aromatic hydrocarbon having a boiling point of 80°–145° C.

4. The process as claimed in claim 3, wherein the solvent is xylene.

* * * * *